United States Patent [19]
Quinn

[11] Patent Number: 6,066,112
[45] Date of Patent: *May 23, 2000

[54] CORPOREAL ACCESS TUBE ASSEMBLY AND METHOD

[75] Inventor: David G. Quinn, Grayslake, Ill.

[73] Assignee: Radius International Limited Partnership, Grayslake, Ill.

[ * ] Notice: This patent is subject to a terminal disclaimer.

[21] Appl. No.: 08/949,381

[22] Filed: Oct. 14, 1997

Related U.S. Application Data

[63] Continuation-in-part of application No. 08/734,630, Oct. 18, 1996, Pat. No. 5,860,952, which is a continuation-in-part of application No. 08/583,930, Jan. 11, 1996, abandoned.

[51] Int. Cl.[7] .................................................. A61M 25/00
[52] U.S. Cl. .............................. 604/93; 604/174; 604/500
[58] Field of Search .................................... 604/264, 523, 604/500, 525, 96, 533, 534, 93

[56] References Cited

U.S. PATENT DOCUMENTS

| | | |
|---|---|---|
| 3,915,171 | 10/1975 | Shermeta . |
| 4,356,824 | 11/1982 | Vazquez . |
| 4,543,089 | 9/1985 | Moss . |
| 4,576,603 | 3/1986 | Moss . |
| 4,594,074 | 6/1986 | Andersen et al. . |
| 4,642,092 | 2/1987 | Moss . |
| 4,666,433 | 5/1987 | Parks . |
| 4,685,901 | 8/1987 | Parks . |
| 4,699,616 | 10/1987 | Nowak et al. . |
| 4,701,163 | 10/1987 | Parks . |
| 4,795,430 | 1/1989 | Quinn et al. . |
| 4,798,592 | 1/1989 | Parks . |
| 4,834,712 | 5/1989 | Quinn et al. . |
| 4,900,306 | 2/1990 | Quinn et al. . |
| 4,932,943 | 6/1990 | Nowak . |
| 4,981,471 | 1/1991 | Quinn et al. . |
| 4,986,815 | 1/1991 | Schneider . |
| 5,073,170 | 12/1991 | Schneider . |
| 5,125,897 | 6/1992 | Quinn et al. . |
| 5,267,967 | 12/1993 | Schneider . |
| 5,267,969 | 12/1993 | Hirsch et al. . |
| 5,308,325 | 5/1994 | Quinn et al. . |
| 5,342,321 | 8/1994 | Potter . |
| 5,370,625 | 12/1994 | Shichman . |
| 5,439,444 | 8/1995 | Andersen et al. . |
| 5,451,212 | 9/1995 | Andersen . |
| 5,484,420 | 1/1996 | Russo . |
| 5,860,952 | 1/1999 | Quinn ........................................ 604/93 |

OTHER PUBLICATIONS

Brochure entitled, "AMT Presents A Giant Step Forward in Innovation The One Step Button," 1 page, published by Applied Medical Technology, Inc.
Brochure entitled, "Innovation is Back, AMT Presents . . . P.R.G.® Gastrostomy Feeding Systems," 1 page, published by Applied Medical Technology.
Brochure entitled, "Stellar Performance," 2 pages.
Brochure entitled, "Polyurethane, Collapsibility, Locking Systems, Flexible Systems," 2 pages.
Brochure entitled, "Introducing EntriStar™ Single Pass P.E.G./J," 3 pages, published by Sherwood Medical.
Brochure entitled, Bard® Silicone PEGs, Bard® Guidewire System & Ponsky™ "Pull" PEG, 1 page, published by Bard.
Brochure entitled, "FLEXIFLO® New Inverta–PEG™ Gastrostomy Kit With Roll–Tip Bumper," 2 pages, published by Ross Products Division, Abbott Laboratories.

*Primary Examiner*—John D. Yasko
*Attorney, Agent, or Firm*—Richard G. Lione; Brinks Hofer Gilson & Lione

[57] ABSTRACT

A corporeal access assembly including a tube segment having a body formed of silicone rubber and containing a coil spring embedded therein. The silicone rubber has a low durometer hardness of about 35 on the A scale. The tube segments have relatively large diameter liquid flow passages therethrough for all French sizes, from 12Fr to 24Fr. The body wall thickness for all French sizes remains the same. An air lumen is provided in one embodiment of the tube segment, with a set connector attached which has a removable plug for blocking or opening an air passage to a retention balloon.

28 Claims, 6 Drawing Sheets

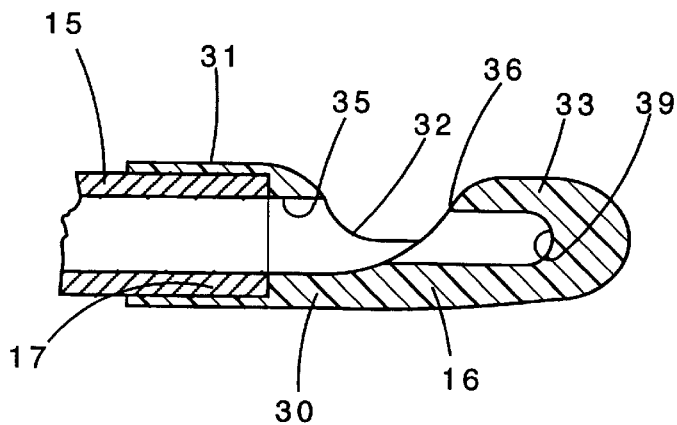
FIG. 3
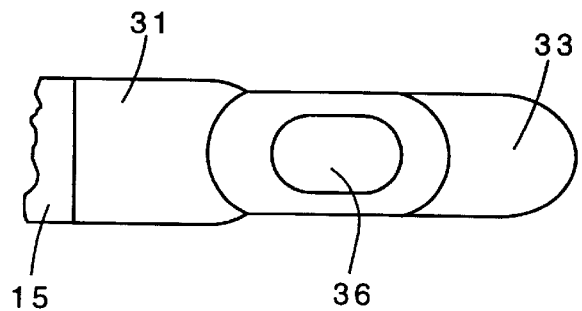
FIG. 4
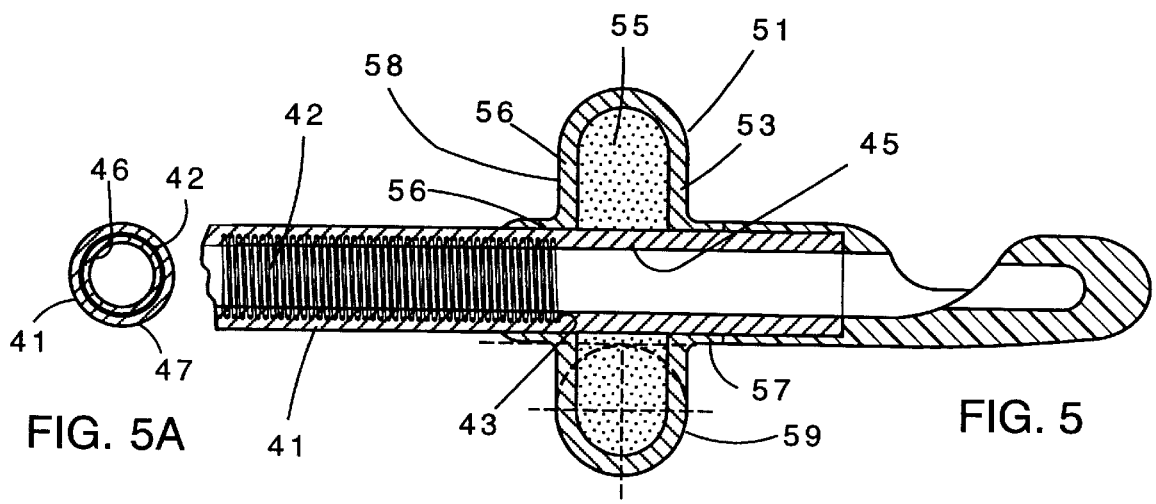
FIG. 5A
FIG. 5

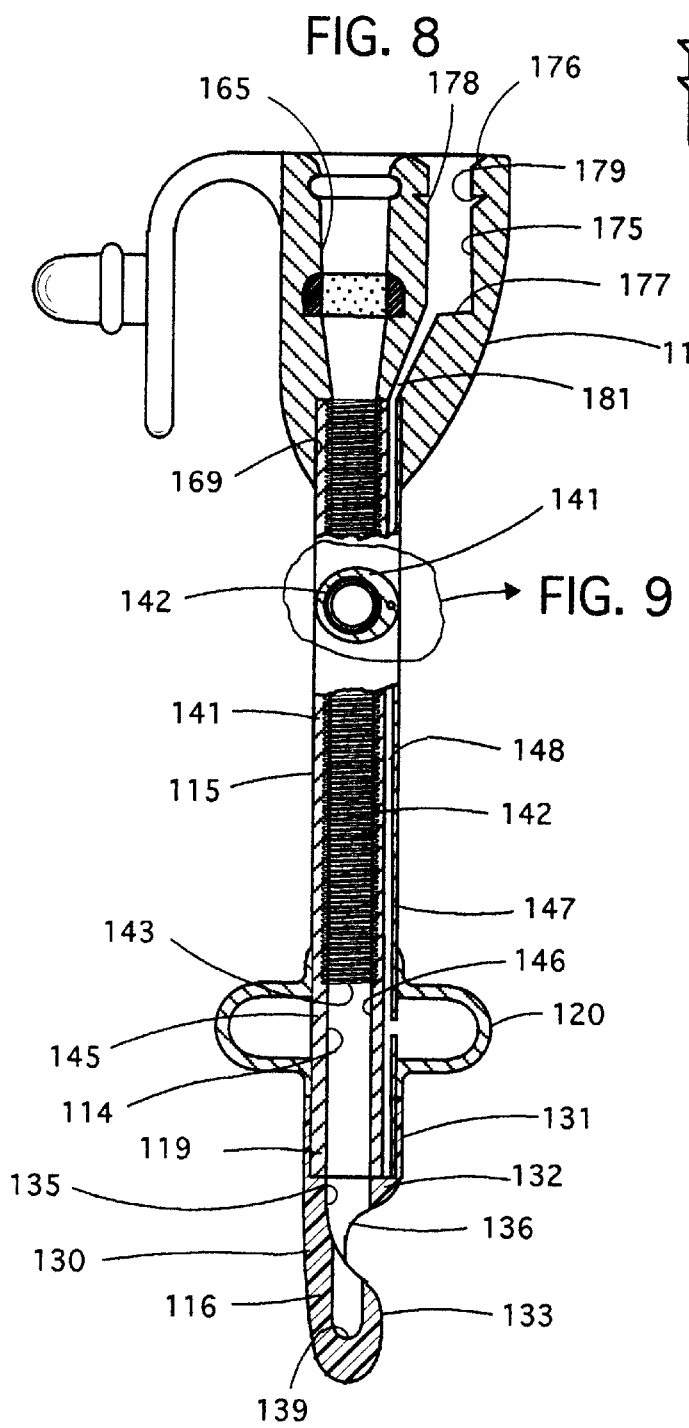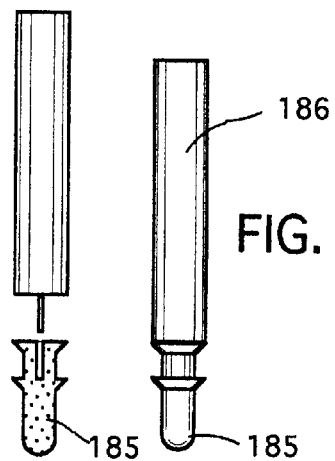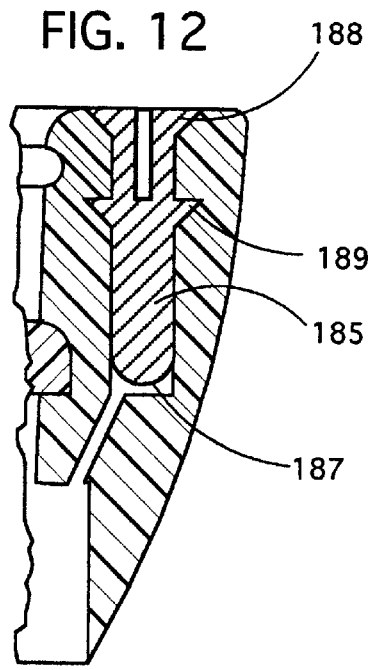

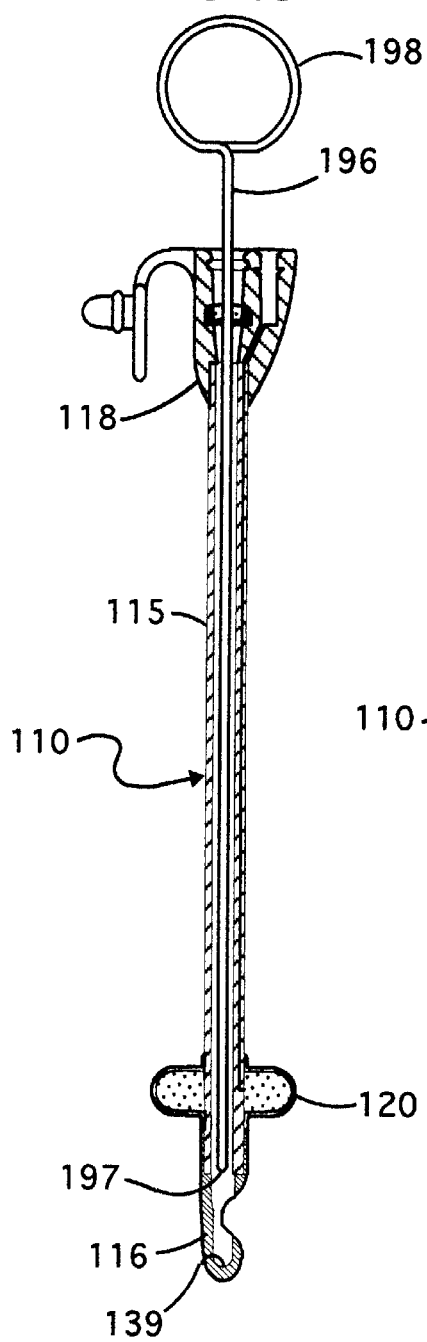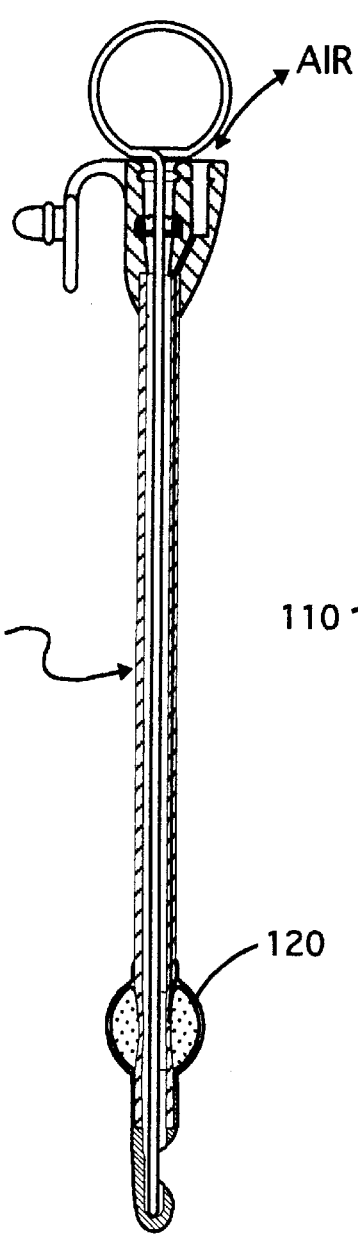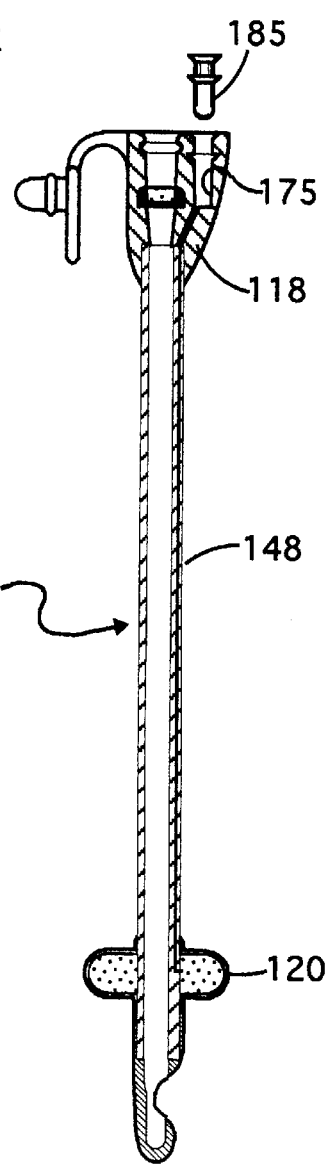

CORPOREAL ACCESS TUBE ASSEMBLY AND METHOD

RELATED APPLICATIONS

This is a continuation-in-part of application Ser. No. 08/734,630, filed Oct. 18, 1996, now U.S. Pat. No. 5,860,952 and entitled Corporeal Access Tube Assembly and Method, which is a continuation-in-part of application Ser. No. 08/583,930, filed Jan. 11, 1996 and entitled Replacement Gastronomy Tube, now abandoned.

FIELD OF THE INVENTION

These inventions relate generally to medical catheters. They relate specifically to catheters which access the stomach and/or intestine, or the bladder, through a stoma or ostomy in the abdominal wall, and maintain a low profile in doing so.

BACKGROUND OF THE INVENTION

The need to artificially introduce food into the gastrointestinal tracts of individuals who cannot eat, or will not eat, has been well known throughout and even prior to this century. Before the mid-1970's, feeding was done nasogastrically with red rubber or polyvinylchloride feeding tubes. The use of enteral feeding by means of nasogastric tubes expanded dramatically in the late 1970's with the introduction of tubes constructed of either silicone rubber or polyurethane. Being constructed of stronger materials, these tubes incorporated thinner walls, and were therefore smaller in outside diameter. These smaller tubes were easier to insert and more comfortable for the patient, and their introduction resulted in a very rapid growth of enteral nutrition via the nasogastric route, and increased interest in enteral nutrition in general.

By the 1980's problems with nasogastric feeding were recognized by clinicians and the advantages of direct gastrostomy access into the stomach through the abdominal wall had been described by Vazquez in U.S. Pat. No. 4,356,824, and by Moss in U.S. Pat. No. 4,543,085. Refinements in securing gastrostomy tubes in the patient were described by Parks in U.S. Pat. No. 4,666,433 and in U.S. Pat. No. 4,685,901.

The 1980's also saw the refinement of methods for forming the gastrostomy stoma. Prior to the 1980's, the stoma or gastrostomy was formed surgically by the Stamm procedure, which required a surgical laporatoratomy to insert the tube, usually a latex urologic Foley retention catheter. A new method, called a "PEG", or Percutaneous Endoscopic Gastrostomy, eliminated the need for a surgical gastrostomy to place the gastrostomy tube and dramatically expanded the interest in the use of direct gastrostomy tubes. The advantages of PEGs and the PEG technique were described by Quinn et al. in U.S. Pat. No. 4,795,430. The word "PEG" is used herein to identify both the tube and the procedure.

Gastrostomy tubes can generally be organized into three main groups, the third of which includes two subgroups:

1. SPECIALTY TUBES placed at the time of gastric surgery by the Stamm technique. The Moss and Vazquez patent tubes are examples of this type.
2. PEG tubes which are used to form the initial stoma or gastrostomy.
3. REPLACEMENT TUBES which are used to replace the PEG tube after a period of time because the PEG has worn out with use, or because a device which is more specific to the patient's need is required. These tubes are inserted into the original stoma created by either the PEG or the Stamm technique. They include:
   a. LOW PROFILE REPLACEMENT TUBES which are preferred for active patients who wish to conceal the tube's outer fitments during periods when they are not receiving feeding formula. The background for this type of replacement tube is described by Quinn et al. U.S. Pat. No. 5,125,897.
   b. SIMPLE REPLACEMENT tubes which are less complicated and less expensive and are used for patients who are not active and have no need to hide their device.

These devices are direct modifications of the original urologic Foley catheters used in early gastrostomies. They are described by Parks in U.S. Pat. No. 4,666,433.

With some exceptions within individual designs, gastrostomy tubes, or tube assemblies (as they will hereinafter be referred to) of the aforedescribed types each incorporate the following seven features or components:

1. A tube to carry the enteral feeding formula into the stomach and/or the intestine.
2. An outflow port in the distal end of the tube. The port or ports may be incorporated in the end or the side wall of the tube. They may also be incorporated in a separate, molded bolus fastened to the distal end of the tube.
3. An administration set connector attached to the proximal end of the tube, which is outside of the patient.
4. A distal end retention device to hold the tube in the stomach, e.g., an inflatable balloon or a molded retention shape which can be deformed with a stylet for insertion and removal.
5. An external bolster to secure the tube at the point where it exits the skin. This bolster maintains the proper distance between the external bolster and the internal retention device, a distance corresponding to the combined thickness of the individual patient's skin, abdominal wall and stomach wall at the site of the gastrostomy.
6. An anti-reflux valve to prevent leakage of gastric acids from the patient when the administration set is being changed or when violent coughing causes excessive back pressure.
7. A measurement system to measure the patient's abdominal wall thickness so that the tube length between the retention device and the external bolster can be adjusted to match this thickness.

Just as gastrostomy tube assemblies are used for enteral feeding, so suprapubic catheter tube assemblies are used to administer drugs to, or drain urine from, the bladder. Such tube assemblies comprise the same seven features or components referred to above in the context of gastronomy tube assemblies. However, they access the bladder through a stoma formed in the abdominal wall above the bladder or pubic area.

Insofar as the construction and operation of the tube segments for such PEG tube assemblies, replacement gastrostomy tube assemblies and suprapubic catheter tube assemblies are concerned, silicone and polyurethane are the materials of choice. Silicone is softer and more compliant than polyurethane. Silicone has a lower modulus of elasticity than urethane. Softness is desirable in medical catheters. However, softness also increases the ability of tube segments to kink and collapse, which are undesirable characteristics. These problems have heretofore normally been addressed by making the silicone rubber walls of the tube segments thicker or by constructing the tube segments from stronger, but less flexible, polyurethane. The designer usually has had to make a choice between a smaller, but less flexible, urethane tube segment and a larger, softer silicone tube segment.

Silicone tube segments including coil springs embedded in the silicone to prevent wall collapse have been used for endotracheal tubes. The use of a coil spring embedded in a silicone rubber wall in such tube segments has served to prevent their collapse, even where relatively soft silicone rubber has been used. For example, in one known instance, a silicone rubber endotracheal tube segment having a wall thickness of as low as 0.075 inches and a Durometer hardness reading of as low as 35A (a discussion of durometer hardness measurements is included in the following description) has been used.

Flexibility and resistance to kinking, as well as resistance to collapsing, are characteristics which are particularly important in gastrostomy and suprapubic catheterization tube segments. Because these tube segments exit the body perpendicular to the skin, it is desirable to be able to bend them to a right angle so that they can lie next to the skin. This problem is addressed in Quinn et al. U.S. Pat. No. 4,834,712. In addition, some forms of gastrostomy tube segments include extensions which feed out of the stomach into the duodenum or jejunum. These tube segment extensions must be able to negotiate from one to five acute angle turns, depending whether they are placed in the duodenum or further into the jejunum. Tube segments with a higher modulus, i.e., less flexible, can dig into the side walls of the intestine and resist making the required tight turns as they move through the intestine.

SUMMARY OF THE INVENTION

A primary object of the present invention is to provide an improved access tube segment for a gastrostomy or bladder access tube assembly, for example, which produces higher flow rates with a softer, more flexible material and, yet, cannot kink or collapse.

Another object is to provide an improved access tube segment for such a tube assembly which minimizes the pull force effect on a stoma in which it is installed.

Still another object is to provide an improved set of access tube segments.

Yet another object is to provide an improved connector for a corporeal access tube assembly.

The foregoing and other objects are realized in accord with the present invention by providing a reinforced silicone tube segment for a stomach or bladder access assembly wherein the tube segment has the same modulus of elasticity as an unreinforced silicone tube segment, yet has walls which cannot be collapsed or kinked. The tube segment has a wall which is approximately the same thickness as a comparable urethane tube but is thinner than conventional silicone rubber tube segments, including reinforced segments. The new tube segment is therefore superior to both urethane and known silicone tube segments used in the aforementioned assemblies.

The tube segment of the present invention is made with relatively soft silicone rubber, i.e., rubber having a hardness of 35 as measured on the standard durometer A scale. For comparison, conventional silicone rubber tubing used in PEG tubes has a durometer measured hardness of 60 on the A scale, a hardness that would be considered medium-to-hard. A hard silicone rubber normally has a durometer measured reading of 80 to 90 on the A scale. Durometer readings are made according to standard practices described in the ASME standard designation D-2240-97, pages 1–4.

The tube assembly of the present invention includes a tube segment having a silicone rubber body with a coil spring embedded in, and extending along, a portion of the tube segment length. The tube segment is fabricated by extruding tubing and inserting a stainless steel coil spring having the same outside diameter as the inside diameter of the tubing. Liquid silicone rubber is then introduced into the tubing so that it flows along the length of the tubing, coating and covering the wire and adhering it to the inside of the tubing. The liquid silicone sets to unitize the tubing, the coil spring and the coating into a tube segment with a generally cylindrical wall having an inner surface defining a liquid flow passage.

A first form of the tube segment embodying features of the invention is made without an inflation/deflation lumen. A second form of tube segment includes a lumen formed in the wall during the conventional extrusion process. As such, the lumen is outside of the coil spring when the tube segment is fabricated.

Regardless which form the tube segment of the tube assembly embodying the present invention takes, it is fabricated in seven (7) different sizes for commercial use: 12 (French) Fr, 14 Fr, 16 Fr, 18 Fr, 20 Fr, 22 Fr and 24 Fr, where "French" sizes are the standard industry size gradations for tube assemblies having different outside diameters. Normal outside diameters (O.D.) for the different French sizes are, for example:

| French Size | O.D. (inches) |
| --- | --- |
| 12 | 0.162 |
| 14 | 0.182 |
| 16 | 0.210 |
| 18 | 0.236 |
| 20 | 0.264 |
| 22 | 0.288 |
| 24 | 0.316 |

Compared to conventional silicone rubber gastrostomy tubes, for example, the tube segments in the tube assemblies of the present invention provide, for the same French size, anywhere from 8% to 66% larger flow area through their internal liquid flow passages. In addition to increased liquid flow capacity for the same (French) size tubes, the tube segments in the tube assemblies of the present invention also have greatly enhanced pull characteristics. Specifically, when a tube in a replacement tube assembly is inadvertently pulled from its set connector end, for example, substantially lower pull force is exerted on the stoma than with conventional tubes, silicone or otherwise. The thin walled tube segments in the tube assemblies of the present invention stretch and absorb the pull force more readily, preventing them from being transmitted entirely to the stoma.

Another aspect of the invention is embodied in an improved set connector for the tube assembly wherein the tube segment contains an inflation/deflation lumen. The set connector is molded separately of silicone rubber. It has an irregularly shaped passage through it which communicates at one end with the inflation/deflation lumen. At the other end, the passage is adapted to receive a corresponding shaped removable plug which can, when called for, create an air tight seal in the passage to prevent deflation of a retention balloon through the lumen.

DESCRIPTION OF THE DRAWINGS

The inventions, including the foregoing objects and advantages thereof, are illustrated more or less diagrammatically in the drawings, in which:

FIG. 3 is a longitudinal sectional view through the bolus end of the replacement tube assembly illustrated in FIG. 1 and 2;

FIG. 4 is a top plain view of the bolus end illustrated in FIG. 3;

FIG. 5 is a longitudinal sectional view, similar to FIG. 3, showing more of the replacement tube assembly embodying features of the inventions;

FIG. 5A is a sectional view taken through the tube assembly of FIG. 5, showing the coil spring;

FIG. 8 is a vertical sectional view taken along line 8—8 of FIG. 7;

FIG. 9 is a horizontal sectional view taken along line 9—9 of FIG. 6;

FIG. 10 is a view, partially in section and partially in front elevation, showing a plug embodying features of the invention and a tool for inserting the plug;

FIG. 11 is a view similar to FIG. 10, with the plug shown mounted on the insertion tool and in full figure;

FIG. 12 is an enlarged sectional view through a portion of the set connector with the plug in place;

FIG. 13 is a sectional view, similar to FIG. 6, of a replacement tube assembly embodying features of the other form of the assembly, with a stylet being positioned in preparation for insertion of the assembly in a stoma;

FIG. 14 is a view similar to FIG. 13 with the stylet positioned for assembly insertion;

FIG. 15 is a view similar to FIGS. 13 and 14 with the stylet removed, the assembly inserted in a stoma, and the air plug about to be introduced;

DESCRIPTION OF THE PREFERRED EMBODIMENT

Figure 1:
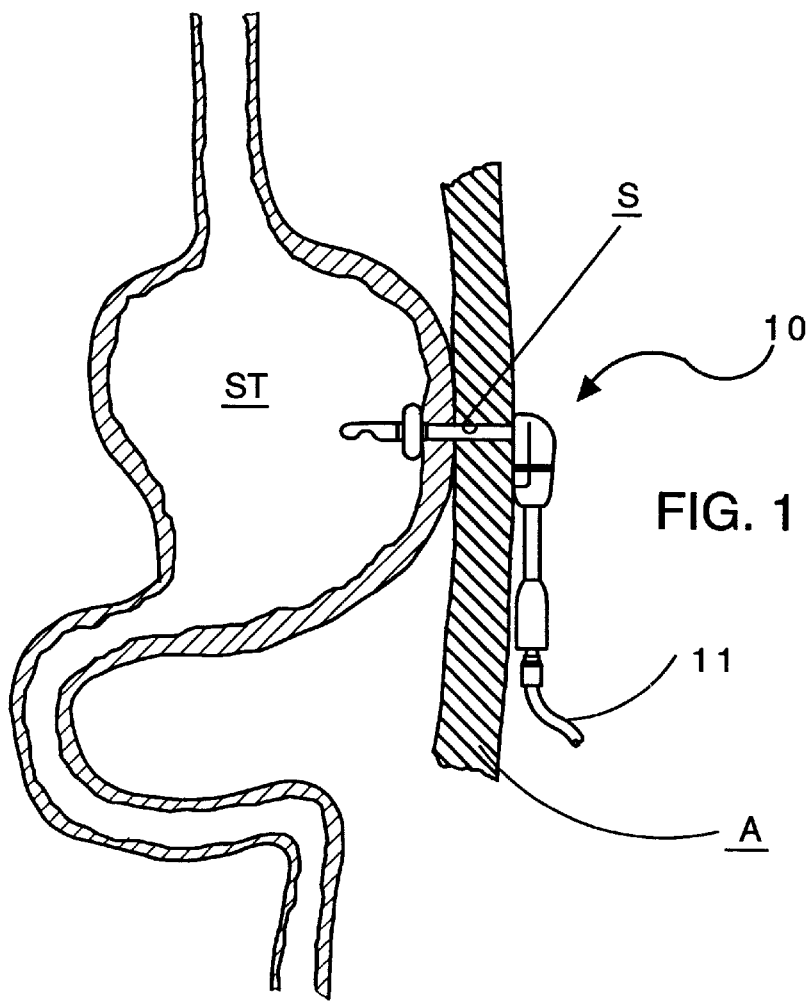
FIG. 1 is an illustration of a replacement tube assembly embodying features of one form of the invention, with the tube assembly in place accessing a patient's stomach.

Referring now to the drawings, and particularly to FIG. 1, replacement a gastrostomy tube assembly embodying features of one form of the invention is shown generally at 10. The replacement gastrostomy tube assembly 10 is shown in place, extending through a stoma S in a patient, from a feeding formula supply tube 11 outside the patient's abdominal wall A to inside the patient's stomach ST. The stoma S may be formed in a conventional manner by one of several well-known procedures hereinbefore referred to.

The tube assembly 10 is a replacement tube assembly in the sense that has hereinbefore been described. The tube assembly 10 is designed to be easily connected to, and disconnected from, a conventional feeding formula supply tube 11 in a manner hereinafter discussed.

Although features of the invention are illustrated here in a gastrostomy tube assembly, those features may find equally advantageous application in PEG and jejunostomy tubes, for example, or suprapubic catheter assemblies, as will hereinafter be discussed.

Figure 2:
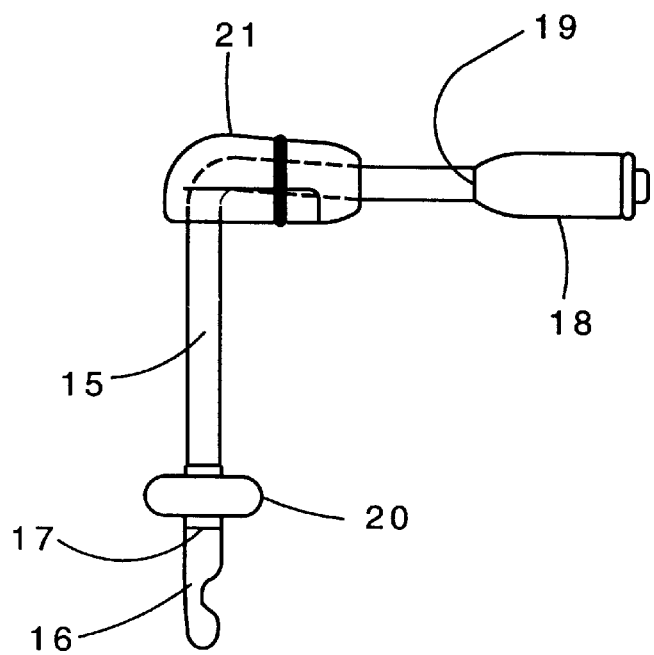
FIG. 2 is an enlarged side elevational view of the replacement tube assembly illustrated in FIG. 1.
Figure 6:
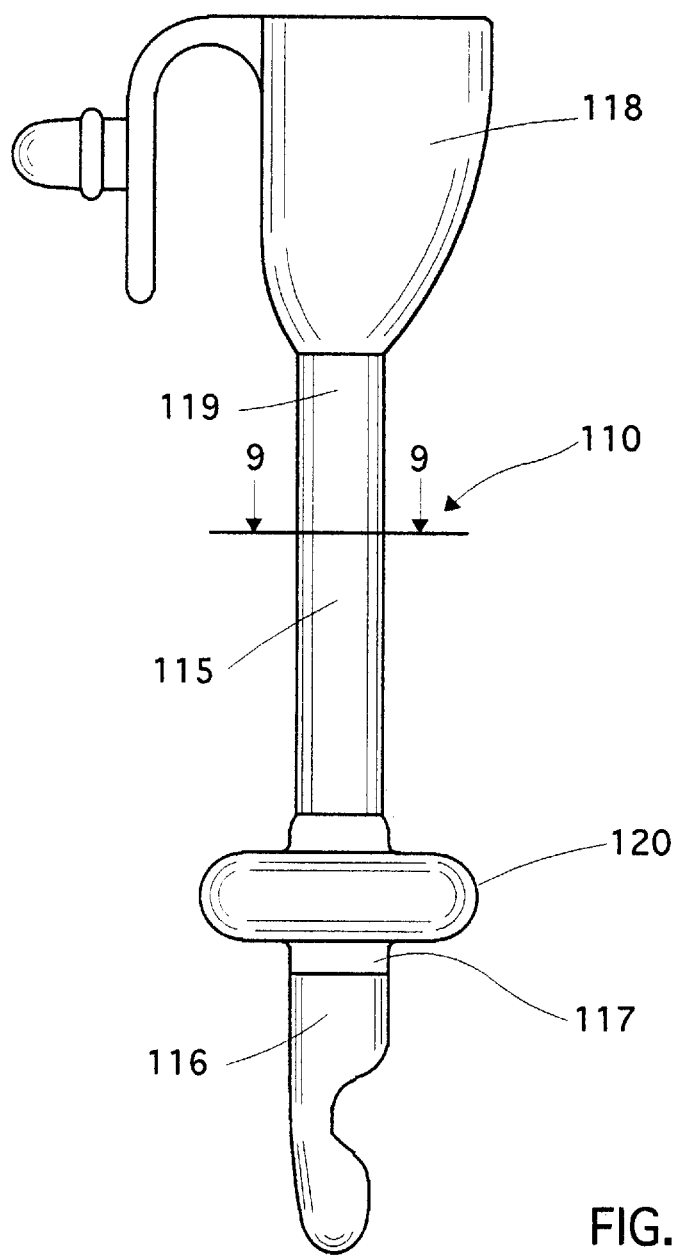
FIG. 6 is a side elevational view of a replacement tube assembly embodying features of another form of the invention.
Figure 7:
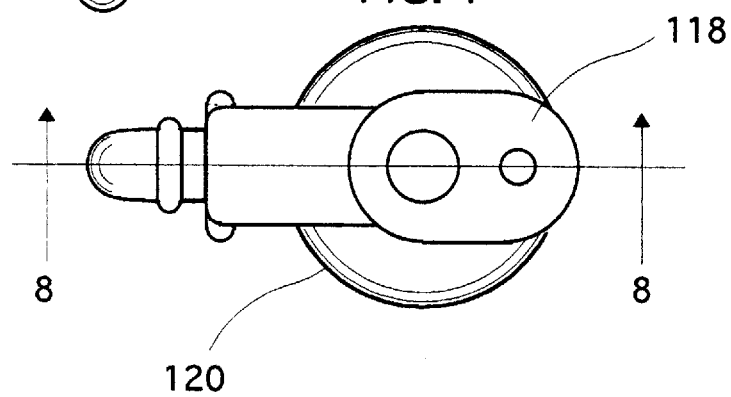
FIG. 7 is a top plan view of the replacement tube assembly shown in FIG. 6.

Referring now to FIG. 2, the replacement gastrostomy tube assembly 10 is seen to comprise a short tube segment 15 formed primarily of silicone rubber and embodying features of the invention. The gastrostomy tube segment 15, which is constructed in a manner hereinafter discussed in detail, has a bolus 16 connected in fluid communication with the liquid flow passage 14 through the tube segment at the latter's discharge end 17, and a set connector 18 connected in fluid communication with the tube segment at the latter's inlet end 19.

Adjacent the bolus tip 16, and encircling the tube segment 15 near the discharge end 17, is a tire-shaped balloon 20. Suffice it to say for purposes of this application that the balloon 20 is filled with a fluid medium such as air or water. Air is preferred and, in the present illustration, is employed.

Approximately intermediate the ends 17 and 19 of the tube segment 15 is a right-angle bolster 21 through which the tube segment passes. The bolster 21 construction and arrangement on the tube segment 15, which comprises a separate invention, grips the tube segment at a selected distance from the balloon 20, and forces the segment into a configuration slightly past a right angle so that the set connector 18 lies immediately adjacent to the patient's abdomen when in place.

Referring now to FIGS. 3 and 4, the bolus 16 and its connection to the discharge end 17 of the tube segment 15 is shown in substantial detail. The bolus 16 may be of the design and construction illustrated and described in the Quinn U.S. Pat. No. 5,451,216, assigned to the same assignee as the present application and invention. The bolus 16 comprises a body 30 having a receiving section 31 for the tube segment 15, a central passage section 32, and a nose section 33.

The tube segment 15, at its discharge end 17, is glued inside the receiving section 31 of the bolus 16 with a silicone based adhesive. A passage 35 extending axially through the passage section 32 of the bolus 16 is then in continuous fluid communication with the passage 14 through the tube segment 15.

A radially extending discharge port 36 is formed through the bolus from the passage 35. It is through this port that enteral feeding discharge takes place.

The nose section 33 of the bolus 16 has an axial, stylet-receiving pocket 39 formed therein. In this sense, the bolus 16 is different than that disclosed in the aforementioned U.S. Pat. No. 5,451,216. The pocket 39 is designed to receive the tip of a stylet (not shown here) in a manner hereinafter discussed in detail, both as to the way the stylet is employed and its purpose.

Referring now to FIGS. 5 and 5A, the portion of the tube segment 15 which joins the bolus 16 is shown in enlarged, longitudinal and transverse sections. The tube segment 15 comprises a silicone body 41 containing a stainless steel wire coil spring 42. The coil spring 42 extends from the receiving end (not shown) of the tube segment 15 to a point 43 immediately adjacent, but not within, the balloon 20. Accordingly, the balloon surrounds a tube segment body portion 45 which is unsupported by the spring 42.

To fabricate the tube segment 15, a coil spring 42 is inserted into an extruded silicone tube. Liquid silicone is introduced into the tube so that it flows the length of the tube, coating and covering the wire of the spring 42 and adhering it to the inside of the tube. The liquid silicone sets to unitize the original tube, the coil spring 42 and the coating into a tube segment 15 having a generally cylindrical wall with an inner surface 46 and an outer surface 47. The coil spring 42 forms what amounts to a skeleton for the silicone body 41 of the tube segment 15.

The silicone tube 41 is initially extruded using raw silicone rubber material and conventional extruding techniques designed to produce a product having high resiliency and low hardness. A low durometer reading of about 35 on the A scale is necessary. In this regard, the silicone rubber used is considerably softer than the 60 durometer (A scale) hardness rubber found in most conventional silicone tubes, and which have been used in endotracheal feeding for many years.

As was previously pointed out, some specialty endotracheal tubes have been used wherein 35 A durometer silicone rubber has been employed, with embedded coil springs as support. These tubes have been larger (25 French or greater) and have had thicker walls (0.075 inches or greater) than the tube segments of the present invention however. Regarding wall thickness of the tube segment 15, that subject will subsequently be discussed.

The balloon 20 is tire-shaped, as has been pointed out. It is formed of a conventional silicone rubber film which is 0.030 of an inch thick in this embodiment. Using the language of vehicle tire construction, it comprises a casing 51 having an outside diameter which varies with French size. The casing 51 has, at its inside diameter which corresponds to the outside diameter of the tube body 41, a pair of beads 52 and 53. The beads 52 and 53 are glued to the outer surface 47 of the tube segment body 41 with a silicone adhesive in a conventional manner.

The balloon 20 is preformed in the shape illustrated. As such, air is trapped in the space 55 when assembled. The beads 52 and 53 are bonded to the tube body 41 to assemble the tube segment 15 and balloon 20.

In the retention balloon 20 on a 14 French size tube segment, for example, the side-walls 56 and 57 of the tire-shaped balloon casing 51 are preferably spaced from each other by 0.200 inches from outer surface to outer surface. The side-wall 56 extends perpendicular to the axis of the tube segment 15 for a distance of 0.100, i.e., it defines a substantially flat outer surface 58 extending outwardly from the bead 52 for 0.100 inches. Connecting the side walls 56 and 57 is the tread wall 59 of the casing 51. It defines a semi-circle in cross-section. The radius of the semi-circle is 0.100 inches.

The aforedescribed balloon 20 configuration provides important advantages. Its flat retention surface 58 is 50% of its diameter defined externally of the beads 52 and 53. In this shape it is very resistant to distortion when functioning in its tube assembly 10 retaining capacity. It also presents a wide, stable, flat retaining surface 58.

According to the invention, tube segments are provided having external dimensions classifying them as 12 Fr. 14 Fr. 16 Fr, 18 Fr, 20 Fr, 22 Fr, and 24 Fr size. These standard external dimensions are hereinbefore set out. The inner surface 46 (which defines the liquid flow passage) of the tube body 41 containing the coil spring 42 in each French size is circular in cross-section. The internal diameters (I.D.) of the flow passages in these tube segments are, according to the invention:

| 12 Fr | — | 0.080 |
| 14 Fr | — | 0.100 |
| 16 Fr | — | 0.118 |
| 18 Fr | — | 0.144 |
| 20 Fr | — | 0.172 |
| 22 Fr | — | 0.196 |
| 24 Fr | — | 0.224 |

Pursuant to the invention the cross-sectional thickness of the tube segment 15 is the same for each French size. In each case, the wire in the coil spring 42 is the same gauge (thickness), i.e. 0.006 inches. Similarly, the cross sectional thickness of the silicone rubber formed by the original tube and the liquid silicone rubber layer which has set inside it is the same for each French size. The original tube thickness is 0.020 inches and the layer of silicone rubber inside the spring 42 is 0.010 inches.

With the tube segment configurations and dimensions illustrated and described, maximum cross-sectional flow area is provided. Nevertheless, the tube segments are resistant to collapse and to kinking, when bent at angles greater than right angles, around short radii. Furthermore, their thin wall, highly elastic characteristics render them resistant to transmission of sudden pull forces to the stoma or retention member while reducing peak pull-out forces when a retention balloon is deflated and pull-out is called for.

Referring now to FIGS. 6–9 a second embodiment of replacement gastronomy tube assembly is shown generally at 110. Like the tube assembly 10 hereinbefore described, the tube assembly 110 is designed to be easily connected to, and disconnected from, a conventional feeding formula supply tube (not shown), in a manner hereinafter discussed.

Once again, the invention is illustrated here in a gastrostomy tube assembly. However, similarly, the invention may find equally advantageous application in PEG and jejunostomy tube assemblies, for example, or suprapubic catheter assemblies.

The replacement gastrostomy tube assembly 110 is seen to comprise a short tube segment 115 formed primarily of silicone rubber and embodying features of the invention. The gastrostomy tube segment 115, which is constructed in a manner hereinafter discussed in detail, has a bolus 116 connected in fluid communication with the liquid flow passage 114 through the tube segment, at the latter's discharge end 117, and a set connector 118 connected in fluid communication with the passage 114 at the latter's inlet end 119.

Adjacent the bolus tip 116, and encircling the tube segment 115 near the discharge end 117, is a tire-shaped balloon 120. The balloon 120 is filled with a fluid medium such as air or water. Again, air is preferred and, in the present illustration, is employed.

Approximately intermediate the ends 117 and 119 of the tube segment 115, a right-angle bolster (not shown) would be mounted. The bolster 21 construction and arrangement on the tube segment 15, hereinbefore discussed, is preferably used.

In FIGS. 8 and 9, the bolus 116 and its connection to the discharge end 119 of the tube segment 115 are shown in substantial detail. The bolus 116 may be of the design and construction illustrated and described in the aforementioned Quinn U.S. Pat. No. 5,451,216, assigned to the same assignee as the present application and invention.

The bolus 116 comprises a body 110 having a tube segment 115 receiving section 131, a central passage section 132, and a nose section 133. The tube segment 115, at its discharge end 117, is glued inside the receiving section 131 of the bolus 116 with a silicone based adhesive. A passage 135 extending axially through the passage section 132 of the bolus 116 is then in continuous fluid communication with passage 114 in the tube segment 115. A radially extending discharge port 136 is formed through the bolus from the passage 135. It is through this port that enteral feeding discharge takes place.

The nose section 133 of the bolus 116 has an axial, stylet-receiving pocket 139 formed therein. In this sense the bolus 15 is different than that disclosed in the aforementioned U.S. Pat. No. 5,451,216, in a manner hereinbefore discussed.

In FIGS. 8 and 9, the tube segment 115 is shown in longitudinal and transverse sections. The tube segment 115 comprises a silicone body 141 containing a stainless steel wire coil spring 142. The coil spring 142 extends from the receiving end of the tube segment 115 to a point 143 immediately adjacent, but not within, the balloon 120. Accordingly, the balloon 120 surrounds a tube segment body portion 145 which is unsupported by the spring 142.

To form the tube segment 115, the coil spring 142 is inserted into an extruded silicone tube. Liquid silicone is introduced into the tube so that it flows the length of the tube, coating and covering the wire and adhering it to the inside of the tube. The liquid silicone sets to unitize the original tube, the coil spring 142 and the coating into a tube segment 115 having a generally cylindrical wall with an inner surface 146 and an outer surface 147.

The silicone tube is extruded with a small diameter, inflation/deflation lumen 148 extending parallel to the passage 114 between the inner surface 146 and outer surface 147. When the liquid silicone sets to unitize the coating, spring 142 and the extruded tube into a unitary wall, the lumen 148 is outside the spring 142, as will be seen.

Referring again to all of FIGS. 6–9, the set connector 118 at the inlet end 119 of the tube segment 115 comprises a fitting 161 which is also molded of silicone rubber. The fitting 161 has a unitarily formed body 162 and cap 163, with the cap flexibly attached to one end of the body by an easily bendable arm 164.

The fitting body 162 also has an axial liquid flow passage 165 formed through it. Seated in the passage 165, approximately intermediate its ends, is an insert 166 containing a conventional slit valve. The valve insert 166 is also molded of silicone and includes a slit 167 which is forced open into a generally round shape by the connector tip on a feeding supply tube (not shown) when the tip is inserted for feeding purposes. When the tip is removed, and the valve 166 is subjected to pressure from below, the valve slit 167 closes.

The inlet end 119 of the tube segment 115 is seated in, and glued with a silicone adhesive to, a generally cylindrical end section 169 of the passage 165 in the fitting body 162. The cap 163, at the other end of the body 162, includes a plug 171 which is received in the passage 165 when it is desirable to disconnect the replacement tube assembly 110 from the feeding tube. An annular locking shoulder 172 is formed on the plug 171 and is adapted to snap fit into an annular locking depression encircling the passage 165.

The set connector body 162 also contains a substantially cylindrical axial passage 175 extending parallel to the passage 165. This passage 175 opens at the attachment end of the set connector 118, in a funnel-shaped face 176. At a point slightly less than one-half the distance between this face 176 and the base 177 of the passage 175, another funnel-shaped face 178 is formed around the passage. This provides an undercut 179, formed above the face 178, as will be seen.

The passage 175 is connected, at its base 177, to the end section 169 of the passage 165, by an inclined passage 181. The passage 181 is positioned so when the inlet end 119 of the tube segment 115 is sealed in the passage end section 169, the passage 181 communicates with the passage 148 in the tube segment 115. As such, it will be seen that the set connector passage 175 is in fluid communication with the inside of the retention balloon 120.

Referring now to FIGS. 10–12, a sealing plug 185 for the passage 175 is shown installed (FIG. 12), seated on its mounting tool 186 in preparation for installation (FIG. 11), and separated from its mounting tool, e.g., after installation (FIG. 10). The plug 185 is molded of silicone rubber in a cylindrical shape corresponding to the passage 175. It has a semi-spherical insertion tip 187 and a frusto-conical sealing collar 188. A frusto-conical locking collar 189 is formed below the sealing collar 188.

The function of, and manner of use, of the plug 185 will be explained in the context of the use of the replacement tube assembly 110. In this regard, attention is invited to FIGS. 13–15 as well as to FIGS. 7–12.

Referring to FIG. 13, a replacement gastronomy tube assembly 110 is shown being prepared for insertion into the patient's stomach through a preformed stoma. A rigid metal stylet 196 of known construction is inserted, tip 197 first, through the set connector 118 into the tube segment 115. The stylet 196 is inserted using its handle 198 until its tip 197 reaches and seats in the pocket 139 of the bolus 116. Further insertion of the stylet then stretches the balloon 120, as seen in FIG. 14.

According to the invention, the stylet 196 is forced into the tube segment 115 until it has stretched the balloon 120 out into the configuration shown in FIG. 14. At this point, the volume of the balloon 120 is actually greater than it is in its relaxed form (FIG. 12) so that a partial vacuum forms within the balloon, causing it to collapse inward to some extent.

With the balloon 120 in a greatly reduced diameter form, the bolus 116 is inserted through the stoma, followed by the balloon and the lower portion of the tube segment 115. As the balloon 120 passes through the stoma it flattens out rearwardly, thus facilitating passage through the stoma. Once the balloon 120 has clearly entered the stomach, the stylet 196 is pulled out. Air enters the balloon 120, permitting it to resume to its normal size and shape as the tube segment 115 under the balloon becomes shorter and its wall thicker again. The tube assembly 110 is then drawn outwardly until the flat surface on the balloon 120 rests against the stomach wall lining.

With the stylet 196 completely removed, the plug 185 is inserted into the bore 175 in the set connector 118. The passage 148 is, thus, sealed off from the atmosphere and air is trapped in the balloon 120, making the balloon more resistant to deformation.

Referring now to FIGS. 16–22, cross-sectional views through seven different size tube segments 115 embodying feature of this invention, and employed in practice, are illustrated. These are 12 Fr, 14 Fr, 16 Fr, 20 Fr, 22 Fr, and 24 Fr tube segments, respectively (identified here as 115-12, 115-14, 115-16, 115-18, 115-20, 115-22 and 115-24). Actual dimensions used in practice for these tube segments are indicated on FIGS. 16 and 17 of the drawings.

Figure 16:
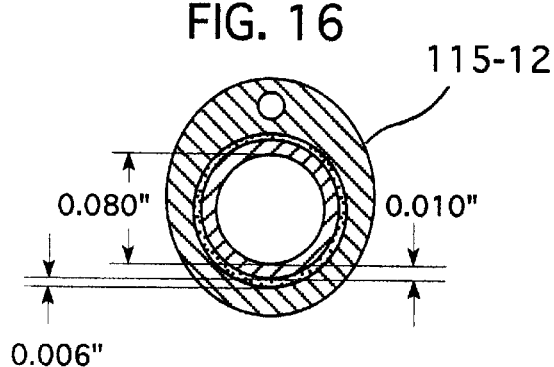
FIG. 16 is a sectional view similar to FIG. 9, but enlarged, showing the 12 French tube segment of the invention and its cross-sectional dimensions.
Figure 20:
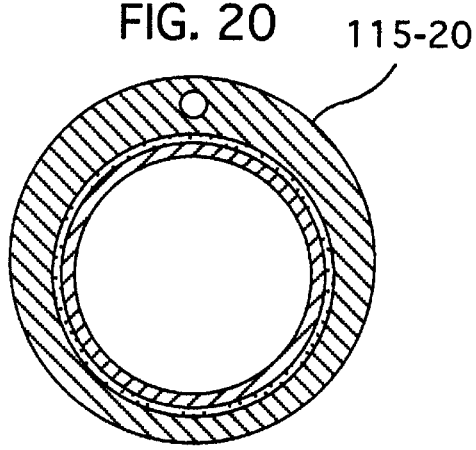
FIG. 20 is a view similar to FIG. 16, but depicting the 20 French tube segment of the invention.
Figure 17:
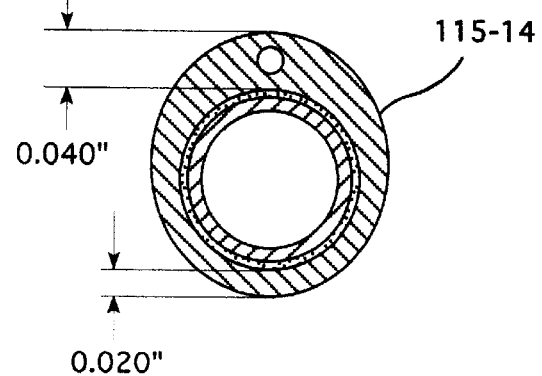
FIG. 17 is a view similar to FIG. 16, but depicting the 14 French tube segment of the invention.
Figure 21:
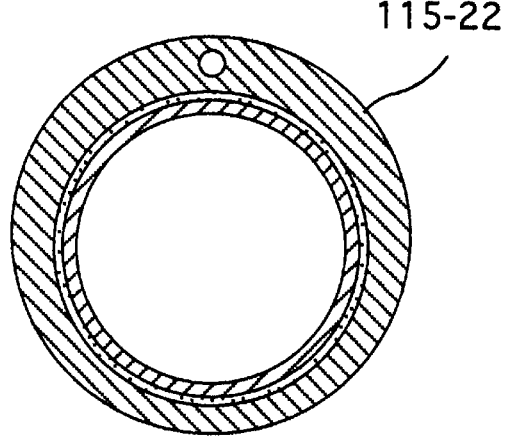
FIG. 21 is a view similar to FIG. 16, but depicting the 22 French tube segment of the invention.
Figure 18:
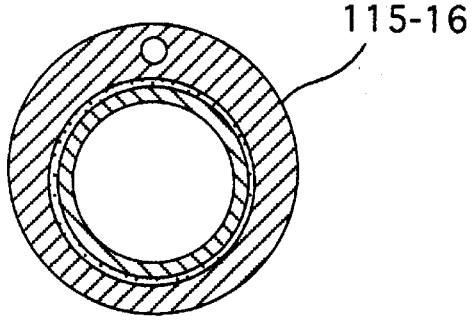
FIG. 18 is a view similar to FIG. 16, but depicting the 16 French tube segment of the invention.
Figure 19:
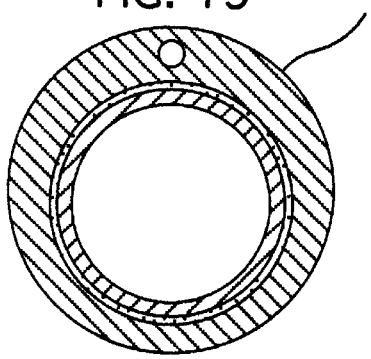
FIG. 19 is a view similar to FIG. 16, but depicting the 18 French tube segment of the invention.
Figure 22:
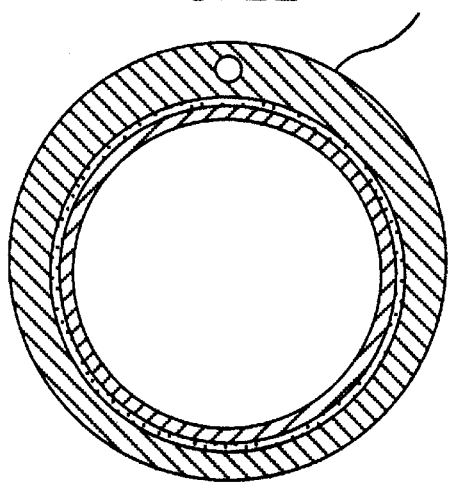
FIG. 22 is a view similar to FIG. 16, but depicting the 24 French tube segment of the invention.

The 12 Fr tube segment shown in FIG. 16 is the same tube segment which is illustrated in FIG. 9. In other words, the FIG. 9 illustration is of a tube assembly 110 incorporating a 12 Fr tube segment.

According to the invention, the 12 Fr tube segment 115-12 is slightly elliptical in cross-section. On the axis which runs through the inflation/deflation lumen 114 it has a diameter of 0.172 inches. On an axis perpendicular thereto, its diameter is only 0.151 inches. The nominal diameter is thus 0.162 inches. The slightly elliptical configuration is necessary to accommodate the lumen 114 in the relatively small 12 Fr tube segment, while still providing a maximum diameter liquid flow passage 114.

The inside diameter of the passage through the tube segment 115-12 is 0.080 inches, as will also be noted. In this regard, it is the same as the inside diameter of the corresponding 12 Fr tube segment 15 hereinbefore discussed.

As will also be seen in FIG. 16, the coil wire thickness is 0.006 inches, the silicone coating thickness inside the coil is 0.010 inches and the basic tube thickness (opposite the lumen) is 0.020 inches. At the lumen, this basic tube thickness increases to 0.040. Thus, the thickness of the composite silicone body and coil spring at its thinnest is 0.036 inches and at its thickest is 0.056 inches.

These dimensions remain constant through each of the other size tube segments, 14 Fr–24 Fr, as the drawings illustrate. Only the outside diameters and inside diameters change. Regarding these outside diameters, the 14 Fr tube segment (FIG. 17) is also slightly elliptical, but the rest of the tube segment sizes are circular.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A corporeal access tube assembly, comprising:
   a) a tube segment having a body formed of soft silicone rubber with a durometer hardness on the A scale of less than 60;
   b) said body including at least one elongated body portion containing a coil spring extending along its length;
   c) said one body portion and said spring forming a generally cylindrical wall having an inner surface defining a liquid flow passage and an outer surface.

2. The corporeal access tube assembly of claim 1 further characterized by and including:
   a) a lumen extending through said one body portion.

3. The corporeal access tube assembly of claim 2 further characterized in that:
   a) said lumen extends through said one body portion outside of said coil spring and inside of said outer surface.

4. The corporeal access tube assembly of claim 1 further characterized in that:
   a) said body includes another body portion which forms a cylindrical wall having an inner surface defining a liquid flow passage and an outer surface, and which does not contain a coil spring;
   b) a retention member is fastened to said outer surface of said other body portion; and
   c) a bolus is fastened to said other body portion, said bolus having a pocket formed therein for receiving the tip of stylet.

5. The corporeal access tube assembly of claim 3 further characterized in that:
   a) said inner surface is cylindrical in cross-section and defines a liquid flow passage through said access tube.

6. The corporeal access tube assembly of claim 5 further characterized in that:
   a) the thickness of said wall at the thinnest point on its circumference is no greater than about 0.036 inches.

7. The corporeal access tube assembly of claim 6 further characterized in that:
   a) the thickness of said wall at the thickest point on its circumference is no greater than about 0.056 inches.

8. The corporeal access tube assembly of claim 7 further characterized in that:
   a) the size of the tube segment is 12 French.

9. The corporeal access tube assembly of claim 7 further characterized in that:
   a) the size of the tube segment is 14 French.

10. The corporeal access tube assembly of claim 7 further characterized in that:
    a) the size of the tube segment is 16 French.

11. The corporeal access tube assembly of claim 7 further characterized in that:
    a) the size of the tube segment is 18 French.

12. The corporeal access tube assembly of claim 7 further characterized in that:
    a) the size of the tube segment is 20 French.

13. The corporeal access tube assembly of claim 7 further characterized in that:
    a) the size of the tube segment is 22 French.

14. The corporeal access tube assembly of claim 7 further characterized in that:
    a) the size of the tube segment is 24 French.

15. The corporeal access tube assembly of claim 7 further characterized in that:
    a) said body is formed of soft silicone rubber with a durometer hardness on the A scale of about 35.

16. The corporeal access tube assembly of claim 2 further characterized in that:
    a) said body is formed of soft silicone rubber with a durometer hardness on the A scale of about 35.

17. The corporeal access tube assembly of claim 3 further characterized in that:
    a) said body is formed of soft silicone rubber with a durometer hardness on the A scale of about 35.

18. The corporeal access tube assembly of claim 4 further characterized in that:
    a) said body is formed of soft silicone rubber with a durometer hardness on the A scale of about 35.

19. The corporeal access tube assembly of claim 5 fixer characterized in that:
    a) said body is formed of soft silicone rubber with a durometer hardness on the A scale of about 35.

20. The corporeal access tube assembly of claim 6 further characterized in that:
    a) said body is formed of soft silicone rubber with a durometer hardness on the A scale of about 35.

21. The corporeal access tube assembly of claim 7 further characterized in that:

a) said body is formed of soft silicone rubber with a durometer hardness on the A scale of about 35.

22. The corporeal access tube assembly of claim 8 further characterized in that:
   a) said body is formed of soft silicone rubber with a durometer hardness on the A scale of about 35.

23. The corporeal access tube assembly of claim 9 further characterized in that:
   a) said body is formed of soft silicone rubber with a durometer hardness on the A scale of about 35.

24. The corporeal access tube assembly of claim 10 further characterized in that:
   a) said body is formed of soft silicone rubber with a durometer hardness on the A scale of about 35.

25. The corporeal access tube assembly of claim 11 further characterized in that:
   a) said body is formed of soft silicone rubber with a durometer hardness on the A scale of about 35.

26. The corporeal access tube assembly of claim 12 further characterized in that:
   a) said body is formed of soft silicone rubber with a durometer hardness on the A scale of about 35.

27. The corporeal access tube assembly of claim 13 further characterized in that:
   a) said body is formed of soft silicone rubber with a durometer hardness on the A scale of about 35.

28. The corporeal access tube assembly of claim 14 further characterized in that:
   a) said body is formed of soft silicone rubber with a durometer hardness on the A scale of about 35.

* * * * *

UNITED STATES PATENT AND TRADEMARK OFFICE
CERTIFICATE OF CORRECTION

PATENT NO.   :   6,066,112
DATED        :   May 23, 2000
INVENTOR(S)  :   David G. Quinn It is certified that error appears in the above-identified patent and that said Letters Patent is hereby corrected as shown below:

On the Title Page

In column 1, item [73], please change "Radius International Limited Partnership" to --C.R. Bard, Inc.--.

Signed and Sealed this

Twenty-fourth Day of April, 2001

Attest:

NICHOLAS P. GODICI

Attesting Officer

Acting Director of the United States Patent and Trademark Office